(12) United States Patent
Fuller

(10) Patent No.: US 9,949,872 B2
(45) Date of Patent: Apr. 24, 2018

(54) THERAPEUTIC EYE AND EYELID COVER

(75) Inventor: Edmund Thomas Fuller, Christchurch (NZ)

(73) Assignee: LABORATORIES THEA, Clermont Ferrand (FR)

( * ) Notice: Subject to any disclaimer, the term of this patent is extended or adjusted under 35 U.S.C. 154(b) by 948 days.

(21) Appl. No.: 14/366,101

(22) PCT Filed: Feb. 21, 2012

(86) PCT No.: PCT/GB2012/000177
§ 371 (c)(1),
(2), (4) Date: Jun. 17, 2014

(87) PCT Pub. No.: WO2012/114066
PCT Pub. Date: Aug. 30, 2012

(65) Prior Publication Data
US 2014/0364927 A1    Dec. 11, 2014

(30) Foreign Application Priority Data

Feb. 22, 2011 (GB) .................................. 1103010.3

(51) Int. Cl.
*A61F 7/00* (2006.01)
*A61F 9/02* (2006.01)
*A61F 7/02* (2006.01)
(52) U.S. Cl.
CPC ............. *A61F 7/00* (2013.01); *A61F 9/029* (2013.01); *A61F 2007/0004* (2013.01); *A61F 2007/0062* (2013.01); *A61F 2007/0292* (2013.01); *A61F 2250/0058* (2013.01)

(58) Field of Classification Search
CPC .............................................. A61F 2007/0004
See application file for complete search history.

(56) References Cited

U.S. PATENT DOCUMENTS

| 3,195,539 | A | * | 7/1965 | Hyman | ..................... A61F 7/08 219/527 |
| 6,641,264 | B1 | * | 11/2003 | Schwebel | ............... A42B 1/247 351/158 |
| 2004/0237969 | A1 | | 12/2004 | Fuller | |
| 2005/0022823 | A1 | | 2/2005 | Davison et al. | |

FOREIGN PATENT DOCUMENTS

DE        102 25 840  A1    12/2003

OTHER PUBLICATIONS

Machine Translation of DE 102 25 840 A1. Retrieved Jul. 7, 2016 from https://translate.google.com/.*

* cited by examiner

*Primary Examiner* — Luther G Behringer
(74) *Attorney, Agent, or Firm* — Ware, Fressola, Maguire & Barber LLP

(57) ABSTRACT

An eye and eyelid cover includes a pair of spaced viewing windows between which, in use, a reservoir of hot water is contained, and a compartment within which a phase change material is contained, the phase change material being molten at the initial temperature of the hot water and solidifying during cooling of the hot water while a treatment procedure is being carried out.

5 Claims, 7 Drawing Sheets

THERAPEUTIC EYE AND EYELID COVER

FIELD OF THE INVENTION

This invention relates to a therapeutic eye and eyelid cover and, in particular, to a device for enhancing tear quality by manipulating the local ocular environment.

BACKGROUND TO THE INVENTION

In British Patent Specification No. 2 384 430, to which reference should be made, there is described a therapeutic eye and eyelid cover which can be fitted against the upper part of the face of the user so as to cover the eyes and eye lids of the user, the eye and eyelid cover including a liquid reservoir and means for saturating or semi-saturating and heating the body of air held in the space between the eye cover and the upper part of the face of the user and to prevent evaporation from, and enhance the heat transfer to, the covered tissue.

It is an object of the present invention to provide an improved therapeutic eye and eyelid cover that can be used to enhance tear quality.

SUMMARY OF THE INVENTION

According to the present invention there is provided an eye and eyelid cover which includes a pair of spaced viewing windows between which, in use, a reservoir of a hot liquid is contained.

This hot liquid as well as maintaining the temperature of the device for treatment crucially heats the viewing windows preventing condensation on the surface of the inner window.

The hot liquid is preferably hot water.

The eye and eyelid cover may include a phase change material. The phase change material becoming molten at the initial temperature of the hot liquid and solidifying or partially solidifying during cooling of the hot liquid whilst a treatment procedure is being carried out. Any phase change material is contained within separate compartments within the device, or encapsulated as separate components placed within the device so that they are exposed to the heat of, but separated from the heating liquid.

The phase change material (PCM) may be a wax or any other material that changes its physical state and has the latent heat characteristics capable of moderating the temperature of the device at any stage of use.

There may also be at least one mechanism such as a porous plug, aperture, or membrane, or other means of permitting the flow of water or water vapour from the reservoir into the space between the cover and the eyes and surrounding tissue upper part of the face of the user.

The preferred features of this device, the hot liquid reservoir, PCM-controlled liquid temperature, and porous plug humidification, result in a range of practical device formats.

These include the following but do not exclude other potential formats a) An opening in the top that allows hot liquid that has been heated by an external means to be poured into the device b) A part line where the body of the device separates, again allowing hot liquid to be poured directly into the device, or a portion of the device to act as a container that can be use to heat the liquid it contains (e.g. placed in a microwave oven). The part line that separates the components prior to use during the hot liquid charging may be horizontal or vertical or along any contour that provides the necessary function c) A device that comes apart to allow one or more components to be heated prior to assembly and subsequent use.

d) A device so arranged that the liquid in the reservoir is heated internally perhaps by induction heating of internal metallic components or direct electrical heating from electric resistance elements e) A device so arranged that the temperature of the liquid in the reservoir is maintained or supported by heat generated within the device by an electrical storage battery or chemical reaction or thermal properties of the components from which it is assembled.

DETAILED DESCRIPTION OF THE PREFERRED EMBODIMENTS

The present invention relates to improvements in and modifications of the invention described in British Patent Specification No. 2 384 430, to which reference should be made to obtain a fuller appreciation of the present invention.

Figure 1:
FIGS. 1, 2 and 3 are schematic views illustrating the use of a device produced using hot water and a heat storage battery.

FIG. 1 shows a tray with a transparent base filled with a measured quantity of water, the side wall of the tray being marked to indicate the level to which the tray should be filled. The water in the tray is heated to boiling by placing the tray in a microwave oven.

Figure 2:
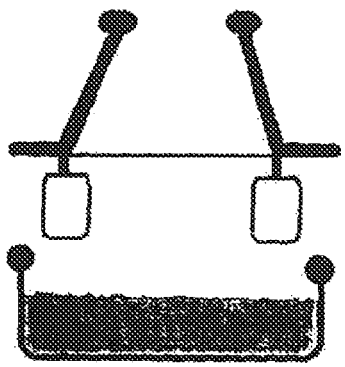

The main body of the treatment device, with a projecting latent heat battery of appropriate design, in then lowered onto the tray of hot water, as indicated in FIG. 2, with the volume of the latent heat battery such that the tray will then be filled, ready for the commencement of a treatment procedure. The latent heat battery may be, for example, a container within which a wax is disposed, the wax having a melting point lower than that of the hot water in the tray but solidifying during cooling of the hot water and thereby modifying the rate of cooling of the treatment device. The initial temperature of the water may be just below boiling point, for example, between 90 and 95° Centigrade. In a typical treatment procedure lasting for several minutes, the temperature may fall to a value of the order of 55° Centigrade, with the Melting Point of the wax of about that temperature.

Figure 3:
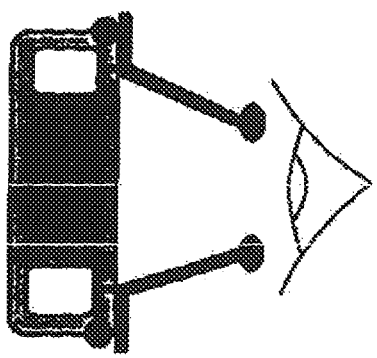

The main body of the device includes those parts required to form a complete eye cover so that, when fitted over the eyes of a person requiring treatment, as indicated in FIG. 3, the base of the tray will extend normally to the person's line of vision.

FIG. 3 does not show the fail-safe clips that are required to hold the tray in engagement with the main body of the device, nor does it show the porous plugs that are provided to permit the flow of water vapour into the space within the eye cover.

Figure 4:
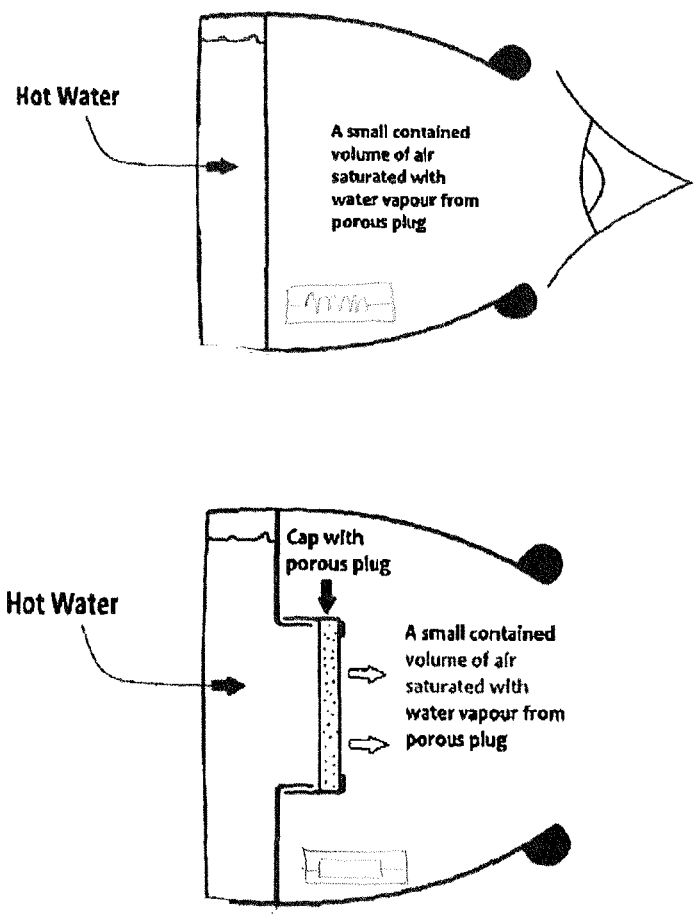
FIG. 4 comprises two diagrammatic cross-sectional views of a device in accordance with the present invention that uses hot water contained between two clear lenses and two caps containing porous plugs.

FIG. 4 shows a modification of the form of goggles described in British Patent Specification No. 2 384 430 in which hot water is used in the interspace between the two lenses. This water can be used as a heat source to heat the whole device to provide sufficient heat to the central area of the inner lens to keep it at a temperature above the saturation temperature of the air/water vapour mix trapped against the face of the user.

FIG. 4 shows in diagrammatic section water heated viewing lenses and vapour plug/cap arrangement.

View 1 (top of FIG. 4) shows twin lenses with hot water filled interspace providing heat for the device and preventing condensation on the inner surface of the inner lens.

View 2 (bottom of FIG. 4) shows device adjacent to the viewing area showing a vapour plug incorporated into the filling cap.

Although, in theory, a fluid other than water could be used as the heat source, the use of water means that it is now possible to provide a supply of water vapour adjacent the eyes of the person being treated by using one or more porous plugs or membranes. Each porous plug or membrane is so fitted that it penetrates the inner lens or body at a location away from the area immediately in front of the eyes so as to provide a clear visual axis. At the same time, the inner surface of each plug or membrane becomes sufficiently damp or allows vapour to penetrate to humidify the air contained by the device against the eyes and face.

Figure 5:
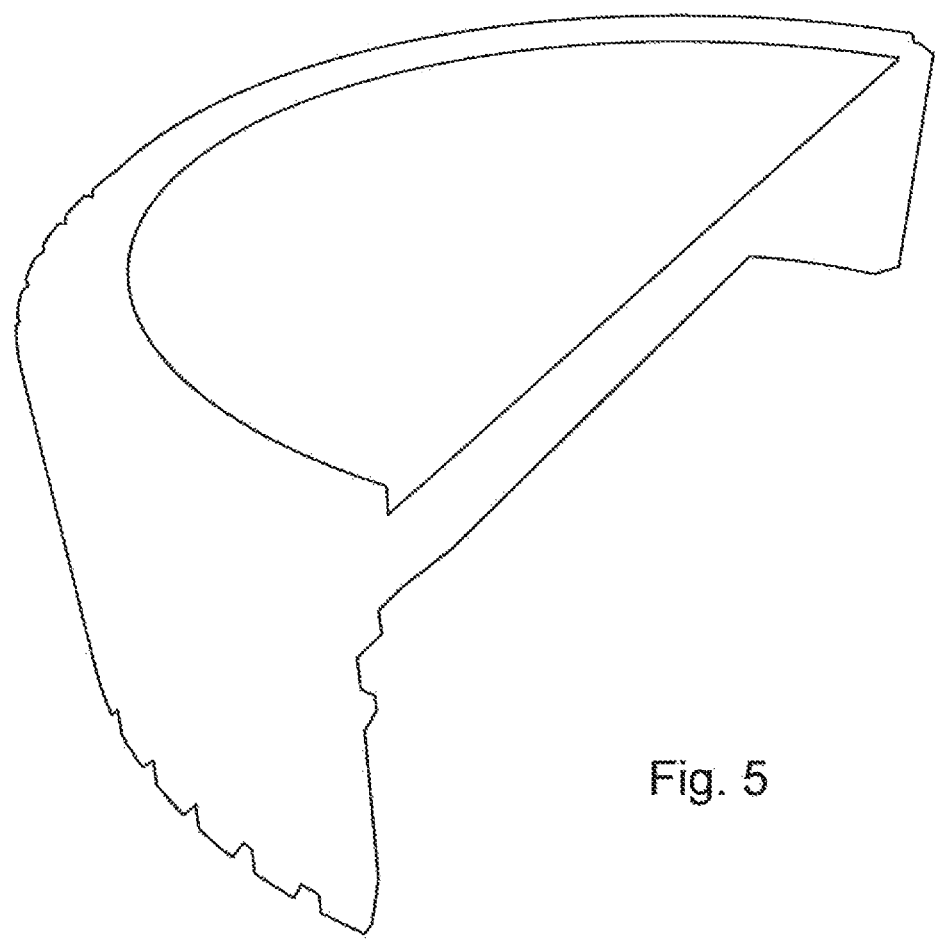
FIG. 5 is a schematic sectional representation of one of the caps shown in FIG. 4.
Figure 8:
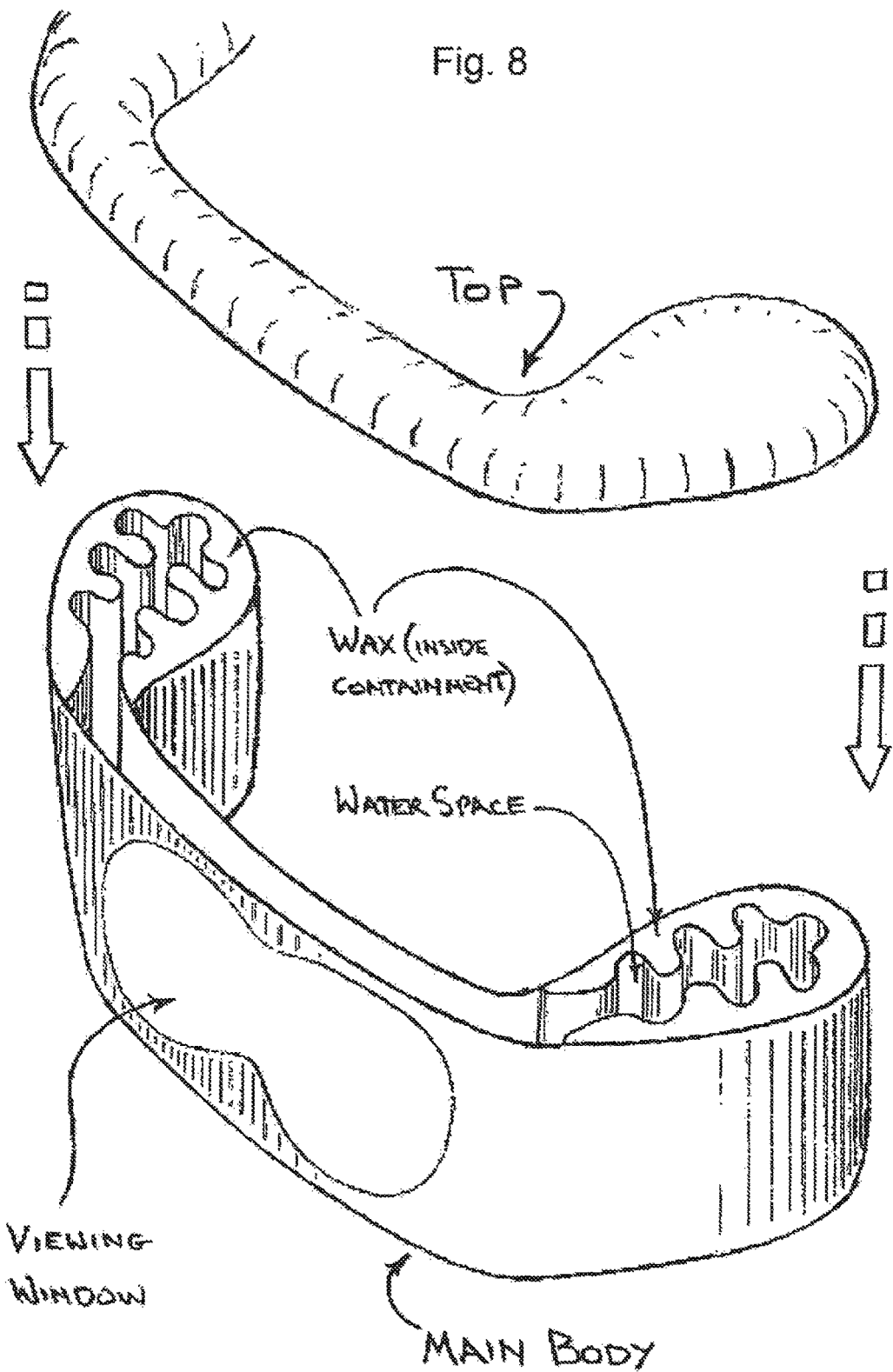
FIG. 8, is a sketch illustrating a device incorporating the use of a hot water filled reservoir and a wax PCM material encased in a separate compartment within the main body and surrounding the reservoir body at each end of the device.
Figure 9:
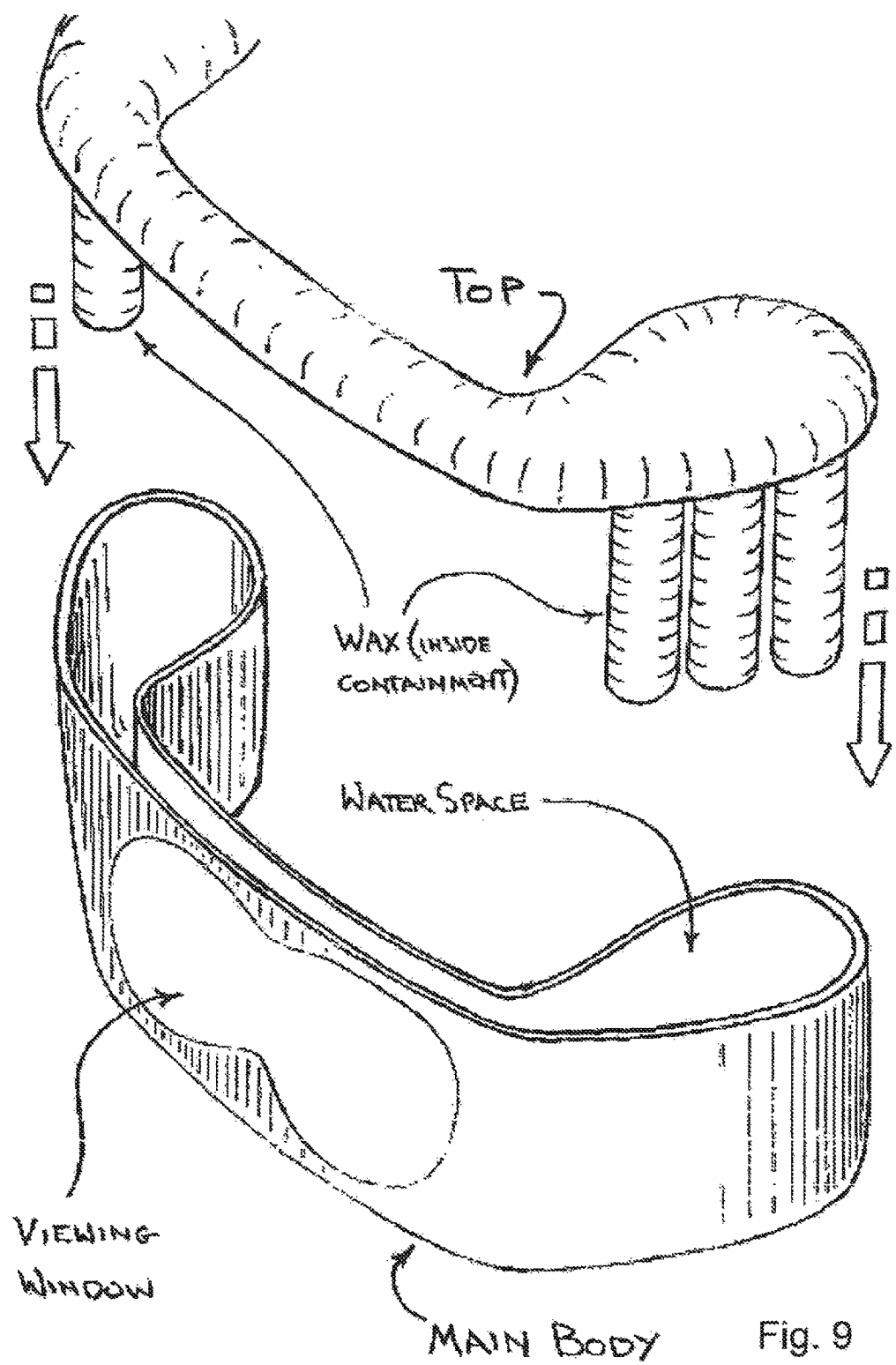
FIG. 9, is a sketch illustrating a device incorporating the use of a hot water filled reservoir and a wax PCM material encased in a sheath suspended from or an integral part of the top.

When water is trapped between the two lenses and the device is not used for some time, it is theoretically possible for the device to become contaminated with microbial growth. FIG. 5 shows a porous plug that can be incorporated into a filling cap. This allows the removal of the porous plug as a routine procedure so that it can, if necessary, be stored in a dry state, while allowing for the ventilation and drying of the remainder of the device. An alternative method for ensuring the inside of the device dries out when not in use is shown in FIGS. 8 and 9 where the whole of the top of the device can be removed.

The porous insert shown in FIG. 5 can be made of a sintered plastics material that only allows water vapour or the quantity of water that can evaporate on the inner or air side thereof to pass through. In some embodiments, the porous plug may be fitted directly into the main body or relevant section of the main body whereas in other arrangements the porous plug may have its own housing which is in some way secured into the device. The body of any plug housing can be made of any suitable plastics material.

In a practical embodiment of the invention, the hot water contained between the two principal components effectively heats the whole device. The porous plugs are snap-fitted into interference-fit formed in the inner shell during the moulding procedure. Large filling ports at each side can be left in the open position when the device is in storage to allow for ventilation and drying of the porous plugs. Alternatively a single filling point that is large enough or may consist of the entire top or other portion of the device that allows for liquid filling and subsequent post use drying of the device may be used, as shown in FIGS. 8 and 9.

Figure 6:
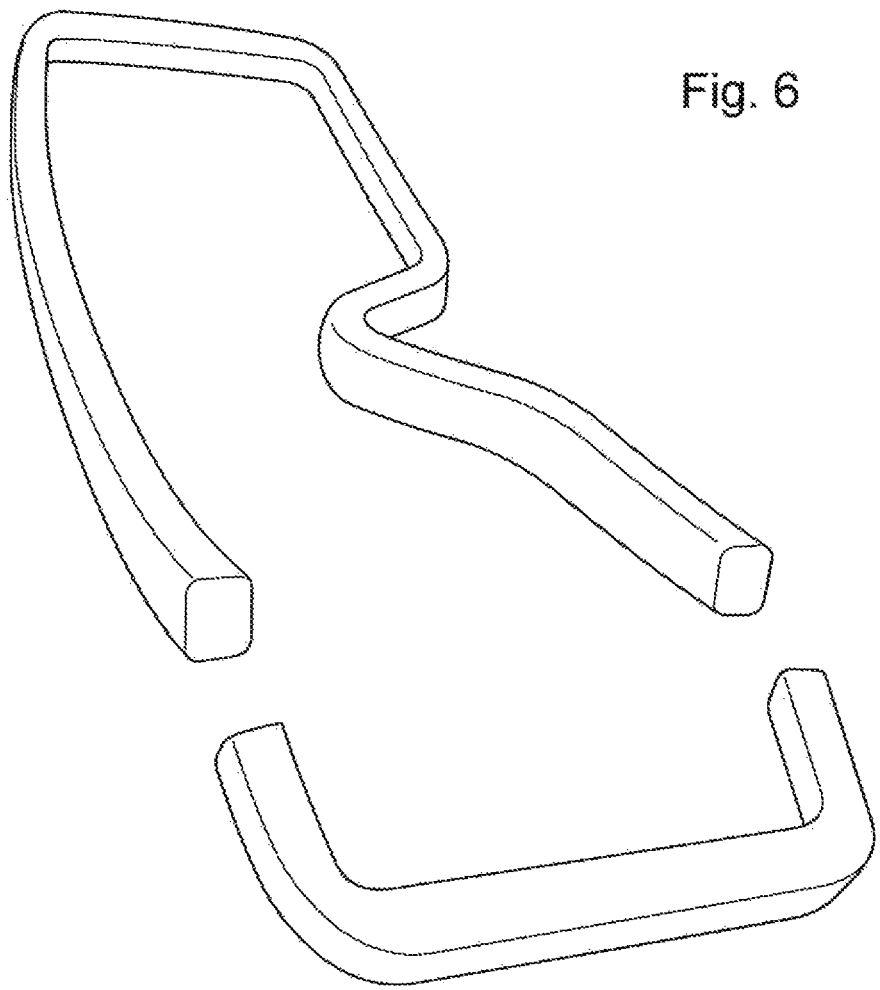
FIG. 6 is a partly sectioned graphical impression of a thin-walled sheath containing paraffin wax.
Figure 7:
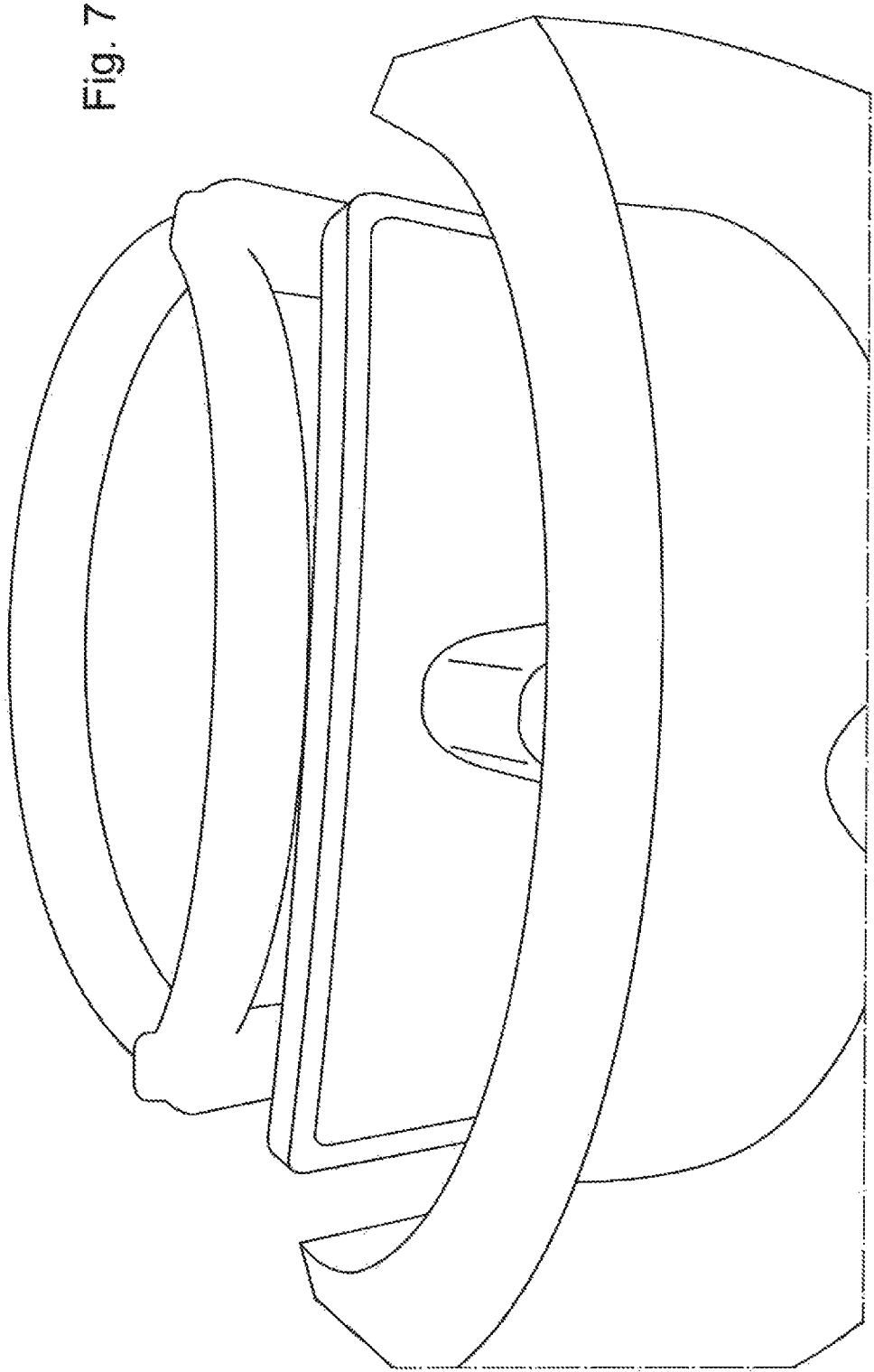
FIG. 7 is a graphical impression showing the thin-walled sheath of FIG. 6 being assembled with other components to form a treatment device.

FIGS. 6 and 7 show how a heat storage mechanism can be incorporated into the design of the device. Paraffin wax is contained within a metal sheath of appropriate configuration. The metallic nature of the sheath and the complex cross-section of the sheath ensure good heat transfer to and from the paraffin wax within the sheath. Paraffin wax is an example of a material having a high latent heat capacity and a suitable melting point making it a very appropriate heat store material for use in this device. Selection of a wax having a suitable melting point (and hence the temperature at which the heat store works) can thus be achieved.

In use, in this example, boiling water is poured into the device, and the water is rapidly cooled by coming into contact with the metal cover of the sheath within which the wax is contained. Most of the wax melts while the water cools to a temperature within the required operating range. In use, the temperature of the water will fall until it reaches the melting point of the wax and the wax will then release its latent heat as it returns to its solid state, reducing the rate at which the water temperature would otherwise fall. This process will continue until all of the wax has returned to its solid state and, by then, the allotted treatment time will be completed and the device will be removed and allowed to go cold.

As an alternative (not illustrated), the device is not heated by being filled with hot water but, instead, has an induction heating arrangement in its base that works in conjunction with the metal casing of the wax heat storage system. This enables the energy to be transferred through the plastic case of the base station and the plastic shell of the device without any direct electrical connections.

FIG. 8 shows an embodiment of the current invention where the PCM or wax necessary to moderate the water temperature is contained within a separate compartment on each side of the device. The corrugated or undulating profile of the inner surface of the containment is intended to enhance the heat transfer and accommodate any dimensional change of the PCM or wax. A smaller cap for filling (not shown) may be incorporated into this removable top. Details of any porous plugs, face seal or head strap are not shown.

FIG. 9 shows the PCM or wax contained in fingers or tubes attached to or integrally moulded into the removable top portion of the device. These heat exchange elements may be of any suitable cross-section or material there function being to separate the water and PCM while allowing adequate heat transfer. Details of any porous plugs, face seal or head strap are not shown.

Significant features of the present invention:—
a) the heat necessary for the therapeutic effect is provided from the energy stored within the device as a result of it being heated or internal battery charged prior to commencement of the treatment operation,
b) a material or materials having specific thermal properties are contained within the device to enhance the capacity of the energy stored within the device,
c) a phase change material of any type having the appropriate phase change temperature and latent heat characteristics may be used,
d) the cover may be heated by internal means, for example, by electrical resistance elements, electromagnetic induction or a chemical reaction,
e) the cover may alternatively be heated by external means, for example, by placing specifically designed parts or all of the cover in a hot environment or heating device or by immersion in a hot liquid,
f) heating may also be effected by supplying a pre-heated liquid to a specifically designated space within the caver.
g) heating may also be achieved during use by discharging an electrical battery included in the eye cover that has been previously charged
h) the cover may include a base station as a separate component that acts as an energy supply to heat the device and/or to charge batteries while the cover is in contact with the base station. This may, if desired, be carried out in a controlled manner based on measurements of the temperature of the eye cover as it is coupled to the base station.
i) the base station may be so connected to the cover as to permit the carrying out of temperature readings. The connection may be either direct or indirect, for example, by induction heating or by means of a radio link,
j) a heated fluid may be circulated through some of the components to heat the cover either prior to use or during use,
k) facilities may be provided to allow for the removal and drying for reuse or replacement of any of the components of the cover,
l) means may be provided to allow for the ventilation and/or drying of any of the components of the cover,
m) a packer may be provided for placement between a seal of the cover and the face of the user, and
n) the seal may be adjustable or replaceable to accommodate different head sizes.

The invention claimed is:

1. An eye and eyelid cover comprising:
a pair of viewing windows, each of said viewing windows configured to extend in front of and across both eyes and eyelids, wherein a reservoir of water is contained between said pair of viewing windows, said eye and eyelid cover comprising one or more compartments or internal components within which a wax phase change material is contained, the wax phase change material being molten at an initial temperature of the water in the reservoir and solidifying during cooling of the water while a treatment procedure is being carried out.

2. An eye and eyelid cover as claimed in claim 1, comprising:
at least one porous plug or membrane permitting the flow of water vapour from the reservoir into a space between a cover and an upper part of a face of a user, said at least one porous plug or membrane being located away from an area corresponding to a visual axis of the viewing windows.

3. An eye or eyelid cover as claimed in claim 1 which can, before and after use be disassembled into two or more constituent parts to facilitate a heating, filling with the water, or post use drying of internal surfaces of said two or more constituent parts.

4. An eye or eyelid cover as claimed in claim 1, wherein the one or more compartments have a corrugated or undulating profile so as to enhance heat transfer to the reservoir of water.

5. The eye or eyelid cover as claimed in claim 1, wherein the wax phase change material is contained in fingers or tubes attached to or integrally moulded into a top portion of the eye and eyelid cover.

* * * * *

UNITED STATES PATENT AND TRADEMARK OFFICE
CERTIFICATE OF CORRECTION

PATENT NO. : 9,949,872 B2  
APPLICATION NO. : 14/366101  
DATED : April 24, 2018  
INVENTOR(S) : Edmund Thomas Fuller Page 1 of 1

It is certified that error appears in the above-identified patent and that said Letters Patent is hereby corrected as shown below:

On the Title Page

Item (73):
Please correct the patent owner's name to read --Laboratoires Thea-- in lieu of "Laboratories Thea".

Signed and Sealed this  
Ninth Day of October, 2018

Andrei Iancu  
*Director of the United States Patent and Trademark Office*